US009632077B2

(12) United States Patent
Hirase et al.

(10) Patent No.: US 9,632,077 B2
(45) Date of Patent: Apr. 25, 2017

(54) DETECTION SYSTEM OF TEST SUBSTANCE

(71) Applicants: TOPPAN PRINTING CO., LTD., Tokyo (JP); TOKYO INSTITUTE OF TECHNOLOGY, Tokyo (JP)

(72) Inventors: Takumi Hirase, Tokyo (JP); Masato Nakayama, Tokyo (JP); Hiroshi Handa, Tokyo (JP); Satoshi Sakamoto, Tokyo (JP); Yasuyuki Naito, Tokyo (JP)

(73) Assignees: TOPPAN PRINTING CO., LTD., Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 14/589,492

(22) Filed: Jan. 5, 2015

(65) Prior Publication Data
US 2015/0125941 A1    May 7, 2015

Related U.S. Application Data

(63) Continuation of application No. PCT/JP2013/068134, filed on Jul. 2, 2013.

(30) Foreign Application Priority Data

Jul. 6, 2012  (JP) ................................ 2012-153054

(51) Int. Cl.
*G01N 33/543*   (2006.01)
*G01N 21/64*    (2006.01)

(52) U.S. Cl.
CPC ..... *G01N 33/54326* (2013.01); *G01N 21/645* (2013.01); *G01N 21/6428* (2013.01)

(58) Field of Classification Search
CPC ........... G01N 33/54326; G01N 21/645; G01N 21/6428
See application file for complete search history.

(56) References Cited

U.S. PATENT DOCUMENTS 5,998,224 A * 12/1999 Rohr ................ G01N 33/54333
                                                            435/7.1
2011/0065209 A1    3/2011  Heil et al.
2011/0183355 A1    7/2011  Handa et al.

FOREIGN PATENT DOCUMENTS

JP        05-052849         3/1993
JP         4179419         11/2008
(Continued)

OTHER PUBLICATIONS

International Search Report mailed Oct. 8, 2013 in corresponding international application PCT/JP2013/068134.
(Continued)

*Primary Examiner* — Sam P Siefke

(57) ABSTRACT

A detection system of a test substance, includes: a magnetic body that is modified by a first substance capable of being bound to the test substance at a first binding site of the test substance; a marker that is modified by a second substance capable of being bound to the test substance at a second binding site of the test substance, the second coupling site being a different site from the first binding site; a development medium that has a flow passage into which liquid, in which the magnetic body and the marker is dispersed, flows due to a capillary phenomenon, the development medium having a detection position for detecting the marker in a portion of the flow passage, the development medium having light transparency at least in the detection position; and a magnetic force generating portion that is equipped in the development medium.

8 Claims, 4 Drawing Sheets

(56) References Cited

FOREIGN PATENT DOCUMENTS

| JP | 4514824 | 7/2010 |
| JP | 4791867 | 10/2011 |
| JP | 2011-257413 | 12/2011 |
| WO | WO 2010/029739 | 3/2010 |

OTHER PUBLICATIONS

Jwa-Min Mam et al: "Nanoparticle-based bio-bar codes for the ultrasensitive detection of proteins", Science, American Association for Theadvancementof Science, US, vol. 301, No. 5641,Sep. 26, 2003 (Sep. 26, 2003), pp. 1884-1886, XP002403223.
Hatakeyama M et al: "Characterization of a magnetic carrier encapsulating europium and ferrite nanoparticles for biomolecular recognition and imaging", Journal Of Magnetism and Magnetic Materials, Elsevier Science Publishers, Amsterdam, NL, vol. 321, No. 10, 2009, pp. 1364-1367.
Extended European Search Report dated Jan. 4, 2016 from European Patent Application No. 13814000.9, 8 pages.

* cited by examiner

DETECTION SYSTEM OF TEST SUBSTANCE

CROSS REFERENCE TO RELATED APPLICATIONS

This application is a continuation application based on a PCT Patent Application No. PCT/JP2013/068134, filed Jul. 2, 2013, whose priority is claimed on Japanese Patent Application No. 2012-153054, filed Jul. 6, 2012, the content of which is hereby incorporated by reference.

BACKGROUND OF THE INVENTION

Field of the Invention

The present invention relates to a detection system of a test substance using a magnetic body and a marker.

Description of Related Art

An ELISA (enzyme-linked immunosorbent assay) method, an MEIA (microparticle enzyme-based immunoassay) method, and the like have been widely used as the method for detecting a small amount of test substance in a sample. However, there are problems that these methods require a long time for operation or reaction, and include complicated measuring operation.

In recent years, an analytic method using immunochromatography has been attracting attention as alternative analytic method to the ELISA method or the like. The immunochromatography is an immunoassay that determines the presence or absence of a test substance. Specifically, the test substance moves in a porous support by a capillary phenomenon, and it is captured by a marker. Then, the test substance is concentrated by contact with a capturing substance locally (for example, a linear shape) immobilized with the porous support. Then, the place where the capturing substance is immobilized is colored.

The immunochromatography is excellent in the light of stable storage, quick measurement, easy determination, and no particular device. Thus, the immunochromatography has been attracting attention as a novel POCT (point of care testing) technique and is used for a pregnancy test and an influenza test In some cases, however, there are cases that the immunochromatography cannot show sufficient sensitivity or cannot detect any markers in some analytical targets. In current immunochromatography, gold nanoparticles have been mostly used as marking substances. However, if the test substance in a sample is extremely low concentration, an erroneous decision to be negative is often encountered by very faint color development due to the insufficient amount of gold nanoparticles accumulated in the test line.

Therefore, researches designed to improve the detection sensitivity of the immunochromatography are being investigated in various research fields.

Patent Document 1 (Japanese Patent No. 4514824) discloses a method of binding of an antibody that recognizes a test substance to a silica nanoparticle containing a fluorescent substance and detection of fluorescence of the silica nanoparticle bound to the test substance.

Patent Document 2 (Japanese Patent No. 4179419) discloses a method of increase of the accumulated amount of a test substance and acquirement of a signal of the test substance by developing a first antibody-bound sensitizer which emits a given signal after development of the test substance and a marking second antibody that recognizes the test substance in the first antibody-immobilized development medium, in the case of low concentration of the test substance.

Patent Document 3 (Japanese Patent No. 4791867) discloses a method of detection of a test substance in short time by binding a first antibody to a magnetic body coated with a noble metal material and by accumulating a complex composed of the test substance and the first antibody-bound magnetic body on a region where a second antibody is immobilized in a development medium using a magnetic force.

Patent Document 4 (Japanese Unexamined Patent Application, First Publication No. H5-52849) discloses a method of specific detection of a substance to be measured, by reacting the substance to be measured in a sample with a substance having a magnetic property and specifically reacting with the substance to be measured, and with a marked substance specifically reacting with the substance to be measured in a position different from that of the substance having a magnetic property, by causing a marked reaction product which has a magnetic property to move by capillary movement, and by capturing the reaction product at a specific position of a capillary movement medium using a magnetic force.

However, Patent Document 1 discloses the method that in the case of low concentration of the test substance, the reaction efficiency between the test substance and the silica nanoparticle decreases, and then, the test substance may be erroneously determined to be negative.

In addition, Patent Document 2 discloses the method that the developing operation and the detecting operation are complicated, and therefore, a long time may be required until the detection result is obtained, due to complicated operations in development and detection.

In addition, Patent Document 3 discloses the method that since a magnetic body which do not form complex with the test substances is accumulated, a cleaning operation may be required and detection of the test substance may be erroneously determined due to the particles which cannot be removed. In addition, Patent Document 4 discloses the method that uses blended yarn fabric of nylon and tetron as a chromatography medium. However, use of such a chromatography medium slows the developing speed of the test substance and the magnetic body which are added to the chromatography medium. In addition, when a color development reaction occurring in the chromatography medium is detected from the outside of the chromatography medium, sufficient sensitivity may not be obtained due to blocking by the chromatography medium.

In the case of the above-described immunochromatography, immobilization of an antibody or an antigen (mostly antibody), which is separately from a marked antibody or antigen and recognizes a test substance, on a development medium is required. Therefore, the development medium that has characteristics not only suitable for capillary development of a sample but also suitable for immobilization of an antibody or an antigen is required. Moreover, there are stringent requirements for the material of the development medium.

Furthermore, in the above-described immunochromatography, the reaction between a test substance and an antibody which is immobilized on the development medium or between a test substance and a marked antibody occurs instantly in the capillary development. Therefore, in order to detect the test substance with high sensitivity, immobilization of an antibody with high binding constant on the development medium is required. The types of antibodies or antigens for immobilization are restricted.

SUMMARY OF THE INVENTION

The present invention was constructed based on such circumstances, and an object of the present invention is to provide a detection system that can promptly and simply detect a test substance in a sample with high sensitivity.

According to an aspect of the present invention, a detection system of a test substance includes: a magnetic body that is modified by a first substance capable of being bound to a test substance at a first binding site of the test substance; a marker that is modified by a second substance capable of being bound to the test substance at a second binding site of the test substance, the second binding site being a different site from the first binding site; a development medium that has a flow passage into which liquid, in which the magnetic body and the marker is dispersed flows by a capillary phenomenon, the development medium having a detection position for detecting the marker in a portion of the flow passage, the development medium having light transparency at least in the detection position; and a magnetic force generating portion that is equipped in the development medium in order to hold the magnetic body in a portion of the flow passage.

In the aspect of the present invention, it is preferable to further include a detection device for detecting light emitted from the inside of the flow passage, in which the marker has a dye.

In the aspect of the present invention, it is preferable that the detection device include a light source which emits light containing excitation light having a predetermined wavelength, a light passage member which irradiates the flow passage with the excitation light, a filter for removing the excitation light, and a detection portion which detects light transmitted through the filter, in which the marker is marked by a fluorescent substance which emits fluorescence by the excitation light.

In the aspect of the present invention, it is preferable that the first substance be selected from a group consisting of an antibody, a fragmented antibody, a complete antigen, a hapten, and an aptamer.

In the aspect of the present invention, it is preferable that the second substance be selected from a group consisting of an antibody, a fragmented antibody, a complete antigen, a hapten, and an aptamer.

In the aspect of the present invention, it is preferable that the marker contain a marking substance selected from a group consisting of a colorimetric substance, a luminescent substance, an enzyme coloring substance, and an oxidation-reduction substance.

According to the present invention, it is possible to promptly and simply detect a test substance in a sample with high sensitivity.

DETAILED DESCRIPTION OF THE INVENTION

Figure 1:
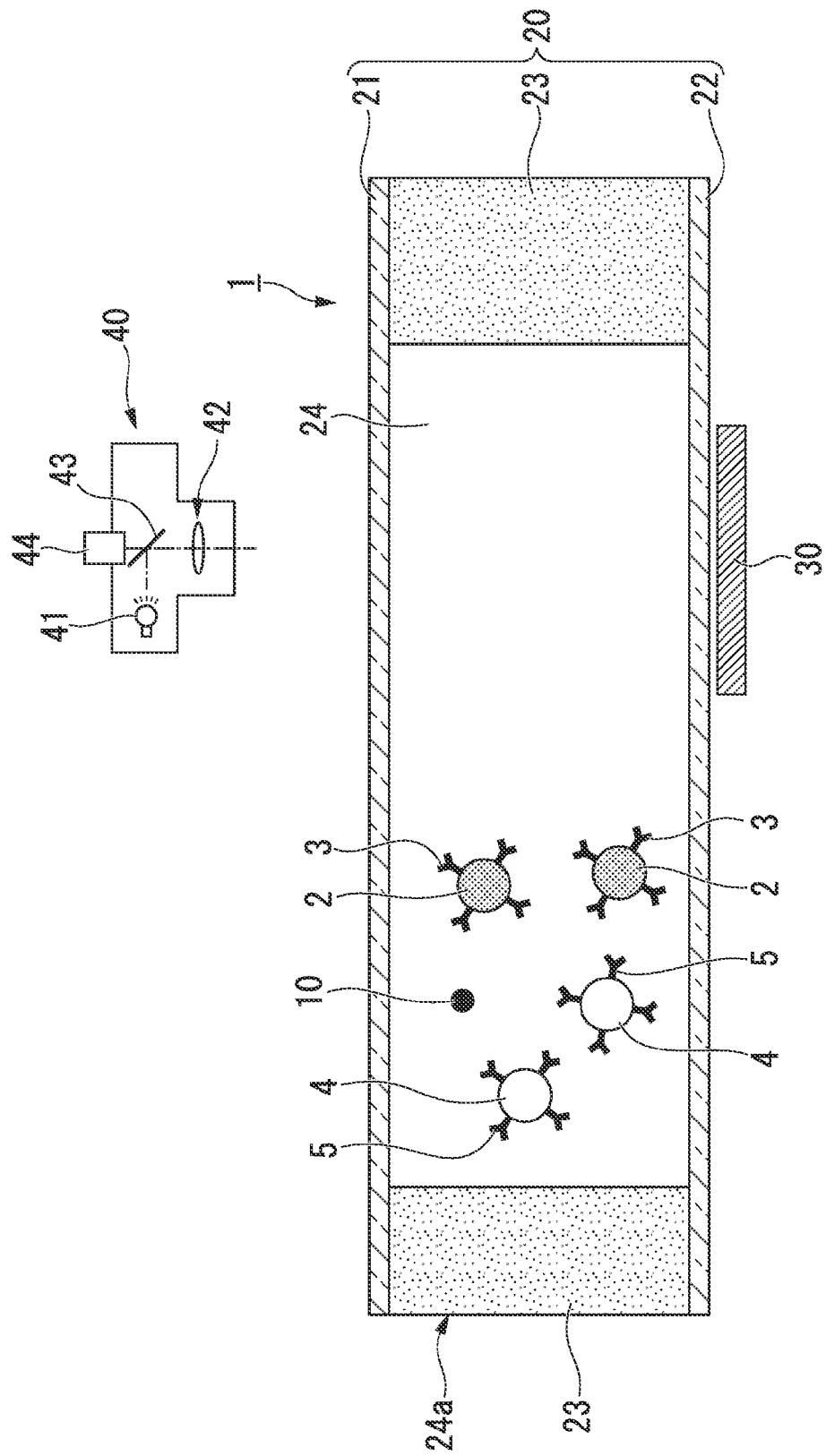
FIG. 1 is a schematic view of a detection system of a test substance according to an embodiment of the present invention.

A detection system 1 of a test substance 10 according to a first embodiment of the present invention (hereinafter, simply referred to as a "detection system 1") is described. FIG. 1 is a schematic view of the detection system 1 of the first embodiment.

Figure 2A:
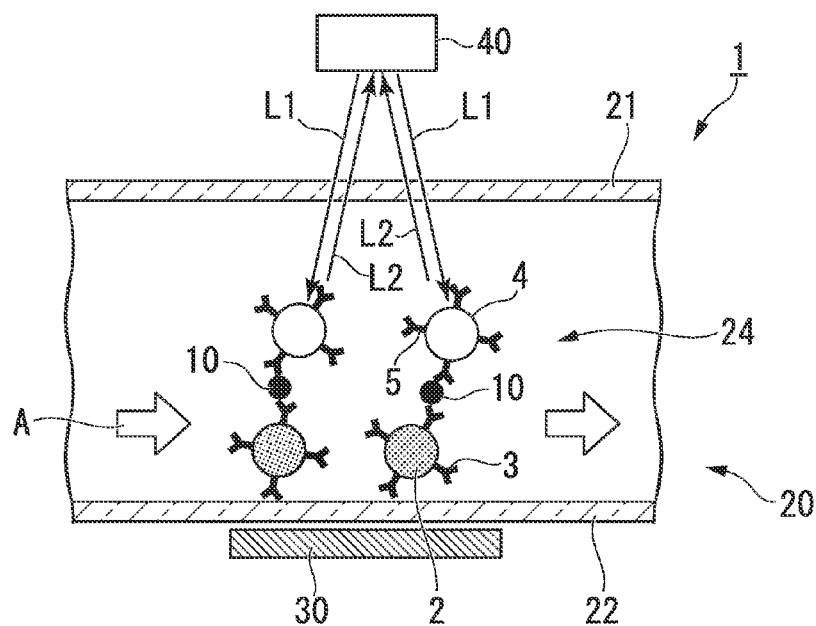
FIG. 2A is a view describing a mechanism of the detection system.
Figure 2B:
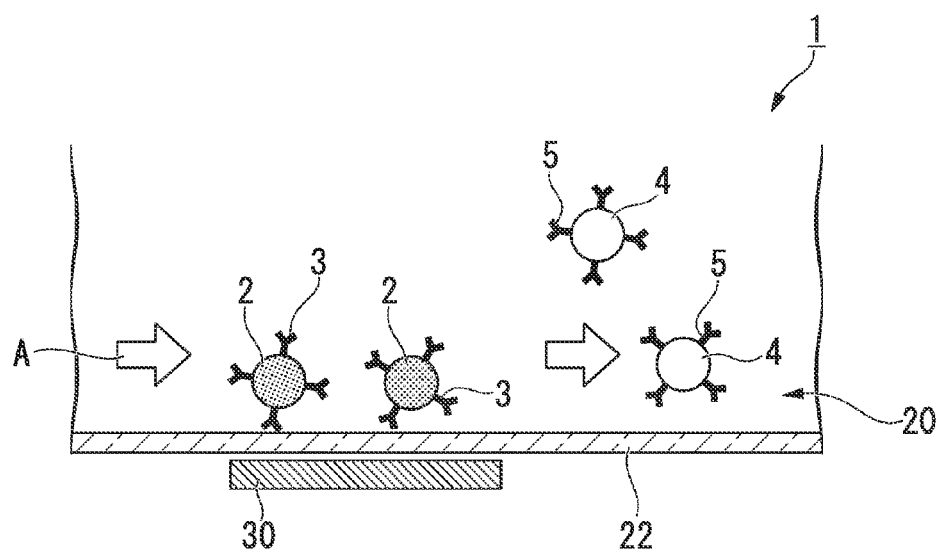
FIG. 2B is a view describing a mechanism of the detection system.

FIGS. 2A and 2B are views showing mechanisms of the detection system 1.

As shown in FIG. 1, the detection system 1 is a system that detects the test substance 10 in a sample. In the first embodiment, it is possible to set all substances including a biological substance and a synthetic substance as the test substance 10. As the sample, it is possible to use an arbitrary sample such as a sample solution derived from a living body such as blood, serum, or urine, and a solution prepared from the sample solution derived from the living body.

The detection system 1 is equipped with a magnetic body 2, a marker 4, a development medium 20, a magnetic force generating portion (magnetic force generating member) 30, and a detection device 40.

The magnetic body 2 is a particle having an average particle size of 20 to 600 nm and is attracted by the magnetic force generating portion 30. That is, the magnetic body 2 is a particle containing a magnet or a soft magnetic body. Preferably, the magnetic body 2 has an average particle size of 60 to 300 nm.

In addition, the magnetic body 2 is modified by a first substance 3 bound to the test substance 10 through a binding site of the test substance 10.

As one example, the magnetic body 2 is a magnetic polymer particle having a magnetic substance and a polymer layer that coats the magnetic substance. The magnetic polymer particle may contain multiple magnetic substances. As the magnetic substance, a ferrite particle such as magnetite capable of producing fine particles in water is preferable. On the other hand, various magnetic metallic fine particles or various magnetic compounds can be used as other magnetic substances other than the ferrite, and it is possible to appropriately use characteristic magnetic properties that these magnetic substances possess.

The first substance 3, which is selected from a group consisting of an antibody, a fragmented antibody, a complete antigen, a hapten, and an aptamer, is employed depending on the test substance 10. The first substance 3 with high specificity to the test substance 10 is preferable. For example, the first substance 3 is easily bound to the test substance 10 and is hard to be bound to a substance which is different from the test substance 10.

In addition, it is preferable that the first substance 3 show a low specificity to the marker 4 itself and a second substance 5 (to be described later). In the first embodiment, the first substance 3 is disposed on a surface of the magnetic body 2. That is, in the first embodiment, the surface of the magnetic body 2 is modified by the first substance 3. The surface-modification may not be adopted as the modification of the magnetic body 2 by the first substance 3.

The marker 4 is a particle, which has an average particle size of 20 to 600 nm, and preferably 60 to 300 nm, and is modified by the second substance 5 bound to the test substance 10 through different site (a second binding site of the test substance 10) from the site (a first binding site of the test substance 10) where the first substance 3 is bound to the test substance 10.

The second substance 5 is a different substance from the first substance 3 and is bound to the different site (the second binding site of the test substance 10) from the binding site (the first binding site of the test substance 10) of the first substance 3 in the test substance 10. The second substance 5, which is selected from a group consisting of an antibody, a fragmented antibody, a complete antigen, a hapten, and an aptamer, is employed depending on the test substance 10. The second substance 5 with high specificity to the test substance 10 is preferable. For example, the second substance 5 is easily bound to the test substance 10 and is hard to be bound to a substance which is different from the test substance 10.

In addition, it is preferable that the second substance 5 show a low specificity to the magnetic body 2 and the first substance 3. In the first embodiment, the second substance 5 is disposed on a surface of the marker 4. That is, in the first embodiment, the surface of the marker 4 is modified by the second substance 5. The surface-modification may not be adopted as the modification of the marker 4 by the second substance 5.

In addition, the marker 4 is a particle such as a polymer carrying a marking substance selected from a group consisting of a colorimetric substance, a luminescent substance, an oxidation-reduction substance, an enzyme coloring substance, and a magnetic substance. The luminescent substances include fluorescent molecules, phosphorescent molecules, chemiluminescent molecules, and enzyme-binding molecules. Hereinafter, in the first embodiment, a case in which the luminescent substance is the fluorescent molecule is described.

A fluorescent rare earth metal chelate complex is preferable as the fluorescent molecule used as the luminescent substance.

The fluorescent rare earth metal chelate complex has characteristics of a long fluorescence life, a large Stokes shift, and a narrow spectral width. With the use of the rare earth metal chelate complex as the fluorescent molecule, it is possible to avoid any background fluorescence noise and to obtain a significantly high fluorescence sensitivity compared to conventional fluorescent molecules. Examples of the rare earth metals constituting the rare earth metal chelate complex showing such fluorescence include europium, samarium, terbium, dysprosium, and the like.

Other fluorescent molecules include DAPI (4',6-diamidino-2-phenylindole), FITC (fluorescein isothiocyanate), GFP (green fluorescent protein), Hoechist, Rhodamine, and the like.

The development medium 20 has a first sheet 21 with light transparency and a second sheet 22 with light transparency, and a spacer 23 which lies between the first sheet 21 and the second sheet 22.

The first sheet 21 is a member formed in a plate shape, a sheet shape, a film shape, or a membrane shape. At least a part of the first sheet 21 has light transparency. Specifically, the first sheet 21 may be an inorganic material such as glass, quartz, ITO (indium tin oxide), and gold, or a polymer material such as polyethylene, polypropylene, polyethylene terephthalate, and cellulose.

The first sheet 21 may have light transparency in a portion where constitutes a flow passage 24 (to be described later). In addition, in the first sheet 21, only a site (a detection position of the first sheet) where a magnetic body 2 is accumulated by the magnetic force generating member may have light transparency.

The second sheet 22 is a member formed in a plate shape, a sheet shape, a film shape, or a membrane shape. At least, a part of the second sheet 22 has light transparency. Specifically, the second sheet 22 may be an inorganic material such as glass, quartz, ITO, and gold, or a polymer material such as polyethylene, polypropylene, polyethylene terephthalate, and cellulose. In addition, the second sheet 22 may have the same material as the first sheet 21 or contain a different material from the first sheet 21.

The second sheet 22 may have light transparency in a part where constitutes the flow passage 24 (to be described later). In addition, in the second sheet 22, only a site (a detection position of the second sheet) where a magnetic body 2 is accumulated by the magnetic force generating member, may have light transparency.

Both the first sheet 21 and the second sheet 22 may have light transparency, or either the first sheet 21 or the second sheet 22 may have light transparency.

That is, the development medium 20 may have light transparency in a direction crossing the flow passage 24 at a position where at least the magnetic force generating portion 30 (to be described later) is disposed.

The spacer 23 holds the first sheet 21 and the second sheet 22 in the state that a space is formed between the first sheet 21 and the second sheet 22. Accordingly, the flow passage 24 that supplies a sample to be analyzed for detecting the presence or absence of the test substance 10 is constructed between the first sheet 21 and the second sheet 22. In the first embodiment, no particular structure is equipped in the flow passage 24. The flow passage 24 is constructed by a plane surface where the first sheet 21 and the second sheet 22 face each other.

The gap between the first sheet 21 and the second sheet 22 is a space that can spread a sample into the flow passage 24 by a capillary phenomenon.

In addition, the plane surface where the first sheet 21 and the second sheet 22 face each other may be subjected to a surface treatment.

The surface treatment on the plane surface where the first sheet 21 and the second sheet 22 face each other is a hydrophilic treatment, a hydrophobic treatment, or the like. Specifically, the plane surface where the first sheet 21 and the second sheet 22 face each other may be subjected to mechanical modification or coating in order to improve its hydrophilicity.

The development medium 20 may employ any shape and structure as long as development by the capillary phenomenon is possible, and the material of the medium is not particularly restricted. For example, a cylindrical member that a cavity corresponding to the flow passage 24 is constructed inside of the development medium 20 may be employed as the development medium 20. In addition, a dry porous member may be employed as the development medium 20. For example, a nonwoven fabric, a filter paper, a polymer film, a porous film or the like can be employed as the development medium 20. In addition, other examples of the development medium 20 include silica, glass wool, cellulose, nitrocellulose, and the like.

The magnetic force generating portion 30 is equipped in the development medium 20 in order to hold the magnetic body 2 in a part of the flow passage 24 placed in the development medium 20. For example, the magnetic force generating portion 30 is a permanent magnet or an electromagnet. In addition, the magnetic force generating portion 30 may be detachable from the development medium 20.

The detection device 40 detects the existence of the marker 4. In the first embodiment, the detection device 40 detects light emitted from the marker 4. Specifically, the detection device 40 equips a light source 41, a light path member 42, a dichroic mirror 43 (a first filter and a second filter), and a detection portion 44.

The light source 41 is, for example, a mercury lamp, a halogen lamp, or a xenon lamp, and emits lights which include excitation lights corresponding to fluorescent molecules. The wavelength of the excitation light may be a wavelength in the ultraviolet region (for example, 200 nm to 400 nm).

The light path member 42 equips the light path in order to irradiate the test substance 10 with the light emitted from the light source 41. In the first embodiment, the light path member 42 irradiates the flow passage 24 with an excitation light. The position irradiated with the excitation light in the flow passage 24 is a detection position for detecting the marker 4 in the first embodiment. In the first embodiment, the detection position for detecting the marker 4 is coincident with the position where the magnetic body 2 in the flow passage 24 is accumulated by the magnetic force generating portion 30.

The dichroic mirror 43 is an optical element which has characteristics that reflect only excitation light among light irradiated to the test substance 10 from the light source 41, and transmit the light having a different wavelength from the excitation light. That is, in the first embodiment, the dichroic mirror 43 has dual functional materials possessing a first filter that reflects only excitation light among light irradiated to the test substance 10 from the light source 41 and a second filter that transmits the light having a different wavelength from the excitation light.

The detection portion 44 has a photomultiplier tube, a CCD detector, or the like, and detects fluorescence intensity.

An operator may determine the intensity of the fluorescence by direct observation of the fluorescence instead of equipment of the detection portion 44.

Next, an operation of the detection system 1 is described together with a detection method of the test substance 10 using the detection system 1.

First, a sample to be analyzed for detecting the presence or the absence of the test substance 10 and a liquid containing a magnetic body 2 and a marker 4 are mixed together.

Next, the mixture of the sample and the liquid is supplied to an inlet 24a in the flow passage 24. Then, the sample spreads in the flow passage 24 toward the direction shown by a reference numeral A in FIG. 2A by a capillary phenomenon. In the flow passage 24, when the sample contains the test substance 10, the magnetic body 2 and the test substance 10 are bound through a first substance 3 and the marker 4 and the test substance 10 are bound through a second substance 5. That is, the magnetic body 2 and the marker 4 are bound through the test substance 10 (refer to FIG. 2A).

When the sample does not contain any test substance 10, the magnetic body 2 and the marker 4 are not bound and exist independently from each other because there is no substance that binds the magnetic body 2 and the marker 4 (refer to FIG. 2B).

The magnetic body 2 in the spread mixture developed in the flow passage 24 is attracted to the magnetic force generating portion 30 by a magnetic force from the magnetic force generating portion 30. That is, the magnetic body 2 bound to the test substance 10 and the magnetic body 2 which is not bound to the test substance 10 are attracted to the magnetic force generating portion 30.

Here, when the test substance 10 is bound to both the magnetic body 2 and the marker 4 (refer to FIG. 2A), the test substance 10, the magnetic body 2, and the marker 4 form a complex, which is attracted to the magnetic force generating portion 30. As a result, the test substance 10 in the spread mixture developed in the flow passage 24 is accumulated together with a marking substance on a portion of the flow passage 24 by a magnetic force from the magnetic force generating portion 30, by the magnetic body 2 bound to the test substance 10.

On the other hand, when the magnetic body 2 and the marker 4 are not bound through the test substance 10 (refer to FIG. 2B), the marker 4 moves to a flow direction (direction shown by reference numeral A in FIG. 2B) of the sample without influence of the magnetic force while the magnetic body 2 is attracted by the magnetic force from the magnetic force generating portion 30.

In addition, since the detection device 40 emits excitation light L1 to the inside of the flow passage 24 (refer to FIG. 2A), the detection device irradiates the marker 4 attracted by the magnetic force generating portion 30 in the flow passage 24 with the excitation light. When the marker 4 is irradiated with the excitation light L1, a given fluorescence L2 (refer to FIG. 2A) emits from a fluorescent molecule that the marker 4 carries. The marker 4 which is not bound to a magnetic body 2 and a test substance 10 moves to the flow direction without influence of the magnetic force. Therefore, the marker is not detected by the detection device 40 due to no existence of the marker 4 at the position of the detection device 40 or due to low contents of the marker 4 below the detection limit of the detection device 40 derived from scattering of the marker 4 in the flow passage 24.

As described above, according to the detection system 1 of the first embodiment, it is possible to detect promptly and simply the test substance with high sensitivity without various and strict conditions used in conventional immunochromatography.

In addition, the flow passage 24 constituted by the first sheet 21 and the second sheet 22 contains a cavity divided by a plane surface where the first sheet 21 and the second sheet 22 face each other. Therefore, the detection sensitivity increases because the test substance 10 is not absorbed to or not captured by a membrane when compared to a case where the sample moves in a porous membrane by the capillary phenomenon.

Generally, the light transparency of the membrane used for the immunochromatography is low.

For this reason, in general immunochromatography, only a portion close to a surface layer of the membrane is set to be detected. In contrast, the first sheet 21 and the second sheet 22 in the first embodiment have high light transparency and can be made transparent. Accordingly, detection of the intensity of light emitted from a marking substance is easier than conventional way and the detection system 1 has high sensitivity.

It is possible to quantitatively determine the test substances 10 based on the magnetic property of the magnetic body 2 attracted by the magnetic force generating member 30 and the fluorescence intensity from the marker 4 if the quantity of the magnetic body 2 and the quantity of the markers 4 are known.

Next, another embodiment of the present invention is described mainly focusing on points different from the above-described first embodiment.

Second Embodiment

According to the second embodiment, a sample which contains a test substance is mixed with a magnetic body and a marker and the mixtures are supplied into a flow passage of a development medium after the lapse of a predetermined time. Accordingly, it is possible to increase the contact time contributing to the binding between the test substance and the magnetic body and the binding between the test substance and the marker compared to the above-described first embodiment. The reaction efficiencies between the test substance and the magnetic body and between the test substance and the marker are improved through such a process, and therefore, it is possible to obtain sufficient sensitivity even in a case where the concentration of the test substance in the sample is low.

Third Embodiment

In the third embodiment, the detection system has a fluorescent dye compound-containing magnetic body disclosed in PCT International Publication No. WO 2010-029739 as a magnetic body, for example. The fluorescent dye compound contained in the fluorescent dye compound-containing magnetic body emits light having a wavelength different from that of the marker described in the above-described embodiments.

For example, the fluorescent dye compound-containing magnetic body has a polymer which has a functional group, which has affinity to a fluorescent substance, on the surface thereof, and a magnetic substance which is disposed in the polymer. It is preferable that the functional group possessed by the polymer be bound to the fluorescent substance and that the polymer and the fluorescent substance form a copolymer.

Examples of such a polymer layer include polystyrene or polyglycidyl methacrylate (poly GMA), and a copolymer thereof. With the use of such a polymer layer, the magnetic body can be bound to another substance through a functional group or the like such as an epoxy group of poly GMA, and thus, it is possible to selectively bind a physiologically active substance and the polymer layer together.

In the detection device, it is possible to perform fluorescence detection on each of the fluorescent dye compound-containing magnetic body and the marker and to calculate the abundance ratio of the fluorescent dye compound and the marker.

In the third embodiment, it is possible to quantitatively determine the content of the test substance if the used amount of the fluorescent dye compound-containing magnetic body and the marker is already known.

Fourth Embodiment

In the fourth embodiment, it is possible to detect each of a plurality of kinds of test substances. That is, a detection system of the present embodiment includes at least a first magnetic body and a first marker for detecting a first test substance and a second magnetic body and a second marker for detecting a second test substance.

The first marker for detecting the first test substance has different optical characteristics from the second marker for detecting the second test substance, for example, the first marker emits fluorescence having a wavelength different from that of the second marker.

It is possible to detect various test substances using a sample by having such a configuration.

In addition, a dye may be used as a second substance modifying the marker instead of the fluorescent mark. In this case, a second substance, which is provided in the first marker for detecting the first test substance, and a second substance, which is provided in the second marker for detecting the second test substance, have dyes of different colors from each other. In this case, the color phase and the saturation at a position of the magnetic force generating member correspond to the quantity ratio and the abundance ratio of the first test substance and the second test substance.

Fifth Embodiment

In the fifth embodiment, the flow velocity of a magnetic body and the flow velocity of a marker in a flow passage are set to be different from each other.

In order to change the fluid rate of the magnetic body and the fluid rate of the marker, the particle size or the hydrophilicity or the hydrophobicity of particles may be changed. In addition, in the fifth embodiment, the flow velocity of the magnetic body is higher than that of the marker in the flow passage.

According to the configuration of the fifth embodiment, the magnetic body reaches the magnetic force generating portion earlier than the marker in the flow passage. Therefore, the marker is easily bound to the magnetic body in a case in which the marker, which reaches the magnetic force generating portion later than the magnetic body, is bound to the test substance. For this reason, the reaction efficiency increases and the detection sensitivity becomes excellent.

In addition, it is possible to control each of the flow velocity of the magnetic body and the flow velocity of the marker by narrowing or widening the space between the first sheet and the second sheet.

Sixth Embodiment

In the sixth embodiment, a pillar configured to retain a sample or configured to stir the sample is provided in a flow passage.

With such a configuration, the same effects as those of the above-described first to fifth embodiments are exhibited. Furthermore, by stirring or retaining the sample, the test substance is reliably captured and the reaction efficiency is improved.

The position of the pillar is not particularly limited as long as it is in the flow passage. For example, it is possible to reduce the flow velocity of the sample in a portion close to the magnetic force generating portion by providing a pillar at a position close to the magnetic force generating portion in the flow passage. Accordingly, the magnetic body is easily attracted by the magnetic force generating portion.

In addition, it is possible to control the flow velocity of the magnetic body or the flow velocity of the marker by changing the hydrophilicity or the hydrophobicity of the pillar.

The configuration for retaining the sample or stirring the sample is not limited to the pillar. For example, an uneven surface constituting the wall surface of the flow passage may be provided on at least one of the first sheet and the second sheet.

Seventh Embodiment

In the seventh embodiment, a stirring unit configured to stir a sample using a magnetic force is provided in a flow passage.

The stirring unit is provided in a portion of the flow passage from a supply port of the sample to the flow passage, to the magnetic force generating portion. A first magnet, which is provided in the portion close to a first sheet and attracts the magnetic body to the portion close to the first sheet, and a second magnet, which is provided in the portion close to a second sheet and attracts the magnetic body to the portion close to the second sheet, are alternately arranged in a flow direction of the sample in the flow passage.

In the seventh embodiment, the contact opportunity between the magnetic body and the test substance is increased and the contact opportunity between the test substance, in a state of being bound to the magnetic body, and the marker is also increased, by the magnetic body advancing by meandering in the flow direction of the sample in the flow passage. Accordingly, the reaction efficiency increases.

In addition, the same effects are also exhibited when an AC magnetic field generating device is provided in a portion of the flow passage from the supply port of the sample to the flow passage, to the magnetic force generating portion, instead of the magnet.

Eighth Embodiment

The eighth embodiment is different from the above-described first to seventh embodiments in that particles for stirring are provided in order to stir a sample in a flow passage.

In addition, a magnetic body, a marker, and particles for stirring are fixed to the portion close to a supply port of a sample to a flow passage by a solid body formed of a water soluble substance. As the water soluble substance for fixing the magnetic body, the marker, and the particles for stirring to the portion close to the supply port of the sample to the flow passage, it is possible to use sugar such as trehalose.

In the eighth embodiment, when the sample is supplied through the supply port of the sample to the flow passage, the water soluble substance is dissolved by water in the sample and the magnetic body, the marker, and the particles for stirring are separated from each other. Then, the particles for stirring stir the mixture of the sample, the magnetic body, the marker, and the particles for stirring.

With such a configuration, it is possible to further improve the reaction efficiency compared to the above-described first to seventh embodiments.

The shape of the particles for stirring is not particularly limited, and may be a shape having unevenness on the surface or an infinite shape.

In addition, the arrangement position of the particles for stirring is not particularly limited as long as it is in the flow passage.

Ninth Embodiment

In the ninth embodiment, the configuration of the magnetic force generating portion for accumulating magnetic bodies in a portion of a flow passage is different from each of the configurations of the first to eighth embodiments.

In the ninth embodiment, the magnetic force generating portion is provided in the portion close to the flow passage such that the magnitude of the magnetic force with respect to the flow passage gradually changes in a certain direction.

Specifically, the magnetic force generating portion is an L-shaped permanent magnet of which the magnetic force gradually increases as the sample goes in flow direction thereof and which has a tip portion protruding to the flow direction of the sample.

In a case of having such a configuration, magnetic bodies are accumulated in the tip portion at which the magnetic force from the permanent magnet becomes strongest. The density of the magnetic bodies is increased by the magnetic bodies being accumulated in the tip portion. That is, the density of the magnetic bodies which are bound to the marker through test substances increases, and therefore, it is possible to increase the detection sensitivity of the test substances.

Tenth Embodiment

In the tenth embodiment, magnetic force generating portions are disposed in both the portion close to the first sheet and the portion close to the second sheet. With such a configuration, it is possible to more efficiently hold magnetic bodies to the magnetic force generating portions.

Eleventh Embodiment

In the eleventh embodiment, the development medium is constituted by a cylindrical capillary and the magnetic force generating portion is a ring-like permanent magnet through which the capillary is inserted.

With such a configuration, the same effects as those of the above-described embodiments are exhibited.

That is, the magnetic force generating portion may have a shape corresponding to the shape of the development medium.

Twelfth Embodiment

In the twelfth embodiment, the detection system has a movable magnet, capable of freely moving in the portion close to the region formed with a flow passage, in addition to the magnetic force generating portions described in the above-described first to eleventh embodiments.

The movable magnet moves along the flow passage, thereby moving a magnetic body by attracting the magnetic body in the flow passage.

For this reason, it is possible to accumulate the magnetic bodies which have not been captured by the magnetic force generating portion using the movable magnet.

Thirteenth Embodiment

In the thirteenth embodiment, the detection system has a plurality of dividable magnets instead of the magnetic force generating portions described in the above-described first to the twelfth embodiments. A state, in which the magnets are disposed at positions separated from each other along a flow passage, is an initial position of the magnets. A mixture of a sample, a magnetic body, and a marker is supplied into the flow passage in the state of the magnets being in the initial position.

In the thirteenth embodiment, magnets are attracted by any of the magnets disposed at the positions separated from each other in the flow passage. Then, the magnets are accumulated by gathering the magnets in a portion of the flow passage.

With such a configuration, the same effects as those of the above-described first to twelfth embodiments are exhibited.

Fourteenth Embodiment

In the fourteenth embodiment, the detection system has means for removing a marker which is not bound to a test substance.

That is, in the fourteenth embodiment, it is possible to reduce a marker which has a possibility of emitting fluorescence of a background in the portion close to a magnetic force generating portion by moving the marker further to the portion close to the downstream than the magnetic force generating portion in a flow direction of a sample in a flow passage.

The means (member or device) for removing the marker may have a water absorption material, a pump, or the like which is provided further in the downstream side than the magnetic force generating portion in the flow passage.

It is possible to reduce autofluorescence caused by liquid components in the flow passage when all of the liquid components in the flow passage are removed by the water absorption material or the pump.

Fifteenth Embodiment

In the fifteenth embodiment, the detection system has switching means (member or device) capable of changing the flow direction of a sample in a flow passage.

The switching means moves a sample, a magnetic body, and a marker from one end (a first end) to the other end (a second end) in a flow passage, and then, moves the sample, the magnetic body, and the marker from the other end (the second end) to the one end (the first end) in the flow passage after switching the direction.

In the fifteenth embodiment, it is possible to cause the sample, the magnetic body, and the marker to approach the magnetic force generating portion again using the switching means after the sample, the magnetic body, and the marker pass through the magnetic force generating portion.

In this manner, in the fifteenth embodiment, it is possible to perform a plurality of times of the binding reaction and the attraction to the magnetic force generating portion using the switching means, and therefore, it is possible to increase the detection sensitivity.

Sixteenth Embodiment

In the sixteenth embodiment, an optical member for making light emitted from a marker incident on a detection portion is provided in a flow passage. That is, the light from the marker reaches the detection portion through the optical member. Therefore, the light condensing efficiency and the detection sensitivity are improved.

As the optical member, it is possible to employ a light guide extending toward the detection portion in the flow passage, a reflective plate which is positioned at an opposite side to the detection portion by interposing the flow passage therebetween and by which the light from the marker is reflected to the detection portion, and the like.

Seventeenth Embodiment

In the seventeenth embodiment, a groove which is formed by being recessed toward the direction in which a magnetic force generating portion is positioned is provided on an inner wall surface of a flow passage. The groove has a size that one complex or a fixed number of complexes formed of a magnetic body, a test substance, and a marker can enter, and a plurality of the grooves are formed by being separated from each other in the flow passage.

In the seventeenth embodiment, it is possible to quantitatively determine the number of complexes formed of the magnetic bodies, the test substances, and the markers by measuring the number of grooves which can detect the emission of light of the marker. In this manner, it is possible to quantitatively determine the test substances in addition to qualitative determination of the presence or absence of the test substances.

Eighteenth Embodiment

In the eighteenth embodiment, a marker is modified by an enzyme that performs enzymatic reaction with respect to a predetermined substrate instead of using a material emitting light. Furthermore, an electrode or a sensor that electrochemically measures the enzymatic reaction is provided instead of the detection devices described in the above-described first to seventeenth embodiments. The electrode in the eighteenth embodiment can be formed of a conductor such as silver, gold, stainless steel, or ITO.

With such a configuration, the same effects as those of the above-described first to seventeenth embodiments are exhibited.

In addition, even in the eighteenth embodiment, it is possible to quantitatively determine magnetic fluids accumulated by the magnetic force generating portion using a magnetic sensor. At least any one of the above-described electrode, sensor, and magnetic sensor may be provided in the eighteenth embodiment.

Hereinbefore, the embodiments of the present invention have been described in detail with reference to the accompanying drawings. However, the detailed configuration is not limited to the embodiments and change of design can be made within the scope not departing from the present invention.

In addition, the components shown in the above-described embodiments can be configured by combining appropriately.

Hereinafter, the present invention will be described in more detail with reference to Examples, but is not limited thereto.

EXAMPLES

Example 1

In Example 1, magnetic accumulation was performed using a magnetic particle for marking which includes a magnetic body and an europium complex as a marking substance, and detection amounts between a case in which a film with high light transparency was used as a development medium and a case in which a nitrocellulose membrane, which is generally used for immunochromatography, was used as the development medium were compared to each other.

Figure 3:
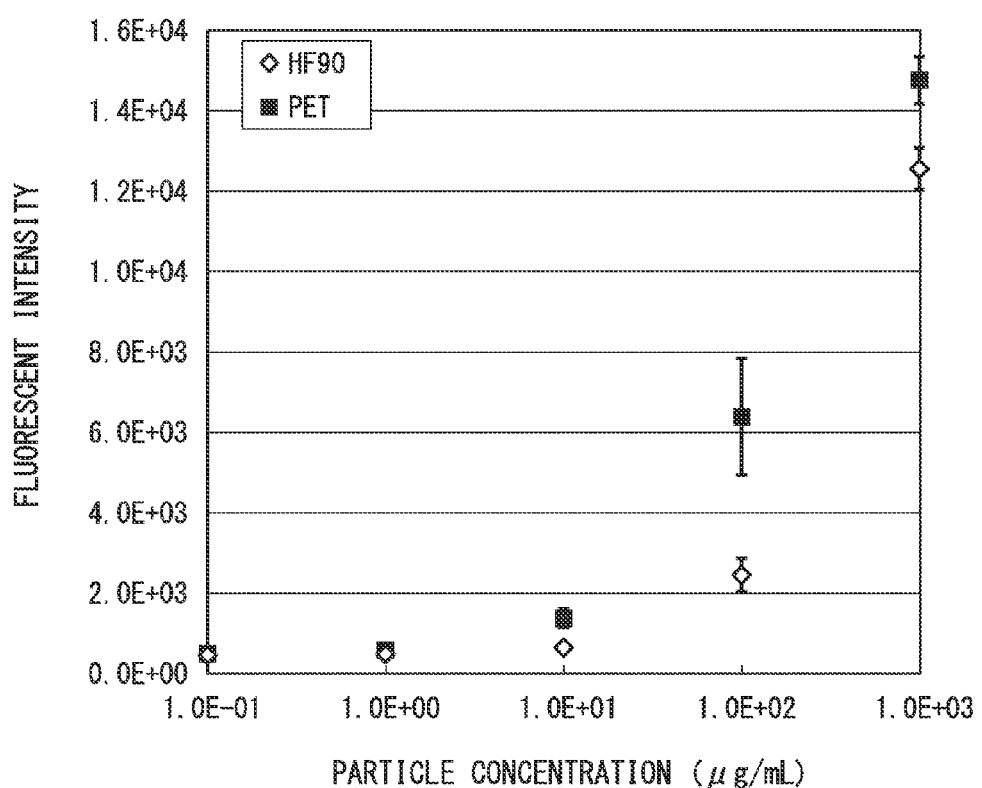
FIG. 3 is an example of an experimental result of the detection system.

Hi Flow Plus membrane 90 (hereinafter, referred to as HF90) was used as the nitrocellulose membrane. A PET film (film thickness: 100 µm) was used as films with high light transparency (member between films) as the first sheet and the second sheet. Magnets were provided under each of the members (HF90 and PET film) and solutions having each of concentrations (0.1 µg/mL, 1 µg/mL, 10 µg/mL, 100 µg/mL, and 1000 µg/mL) of the magnetic particles for marking were added dropwise by 10 µL. In the PET film, a second PET film as the second sheet was superimposed on the droplet which was added dropwise on a first PET film as the first sheet. In each of the cases of using HF90 and the PET film, fluorescent color development of the magnetic particles for marking at a magnet installation position was detected using a CCD detector by being irradiated with a xenon lamp, and digitization was performed. The results are shown in FIG. 3.

With the results from Example 1, it was possible to confirm concentration dependency with respect to the fluorescent intensity up to a particle concentration of 10 µg/mL in the fluorescent intensity when using the first PET film and the second PET film. In contrast, it was possible to confirm concentration dependency only up to 100 µg/mL when using HF90 and it was impossible to confirm concentration dependency with respect to the fluorescent intensity in the concentration of lower than or equal to 10 μg/mL.

As described above, in the case of using the first PET film and the second PET film (in the case of using a member between films), it was confirmed that it is possible to detect a tenth of the magnetic particles for marking compared to the case of using the membrane. It became possible to detect the fluorescence in a low concentration region, in which it was impossible to detect the fluorescence through general immunochromatography, through a detection method in the magnetic accumulation and between the films.

Example 2

In Example 2, a test for detecting a test substance was performed using prostate-specific antigen (PSA), which is a bio-marker of prostatic cancer, as the test substance. A monoclonal antibody (a first anti-PSA antibody), which recognizes PSA, was used as the first substance. A monoclonal antibody (a second anti-PSA antibody), which recognizes a different portion from that recognizing the first substance of PSA, was used as the second substance. In addition, the first anti-PSA antibody was bound to the surface of a magnetic particle, and an anti-PSA antibody-modified magnetic particle was obtained. Furthermore, the second anti-PSA antibody was bound to the surface of a marking particle containing a europium complex as a fluorescence marking substance, and an anti-PSA antibody-modified marking particle was obtained.

Figure 4:
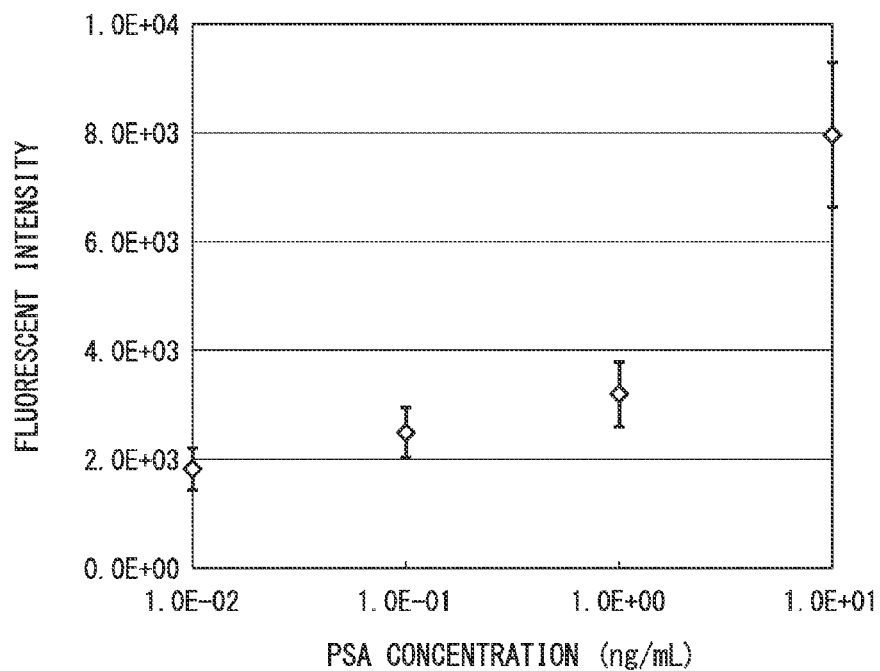
FIG. 4 is an example of an experimental result of the detection system.

A medium between glasses with a gap, on which a micro cover glass and a cover glass with a gap (thickness of the gap: 20 μm) were superimposed, was used as the development medium. A magnet was provided under the medium between glasses with a gap, and mixed solutions, in which an anti-PSA antibody-modified magnetic particle solution, an anti-PSA antibody-modified marking particle solution, and antigen solutions (PSA solutions) at each of concentrations (PSA concentrations: 0 ng/mL, 0.01 ng/mL, 0.1 ng/mL, 1 ng/mL, and 10 ng/mL) were mixed for 10 minutes, and were added dropwise by 20 mL between the gap glasses. Then, magnetic accumulation was performed and complexes formed of the anti-PSA antibody-modified magnetic particles, PSA, and the anti-PSA antibody-modified marking particles were accumulated. Five minutes after the start of the magnetic accumulation, the contents of the space between the gap glasses were substituted with 30 μL of PBST (phosphate buffer solution to which 0.05% Tween 20 is added). Then, the complexes at a magnet installation position were irradiated with a xenon lamp, fluorescent color development obtained by the complexes was detected using a CCD detector, and digitization was performed. The results are shown in FIG. 4.

Comparative Example 1

In Comparative Example 1, a test for detecting a test substance was performed through immunochromatography in the related art using the same PSA and the anti-PSA antibody as those in Example 2. A first anti-PSA antibody was applied to a region corresponding to a test line in which Hi Flow Plus membrane 120 (hereinafter, referred to as HF120) was used as the nitrocellulose membrane, and an anti-mouse IgG antibody was applied to a region corresponding to a control line. Thereafter, blocking and washing were performed to obtain an antibody-immobilized membrane.

In addition, a coupled pad containing an anti-PSA antibody-modified magnetic marking particle was obtained by drying a magnetic particle for marking, which was obtained by binding a second anti-PSA antibody to the surface of a magnetic particle containing a europium complex as a fluorescence marking substance, in a glass fiber pad.

Figure 5:
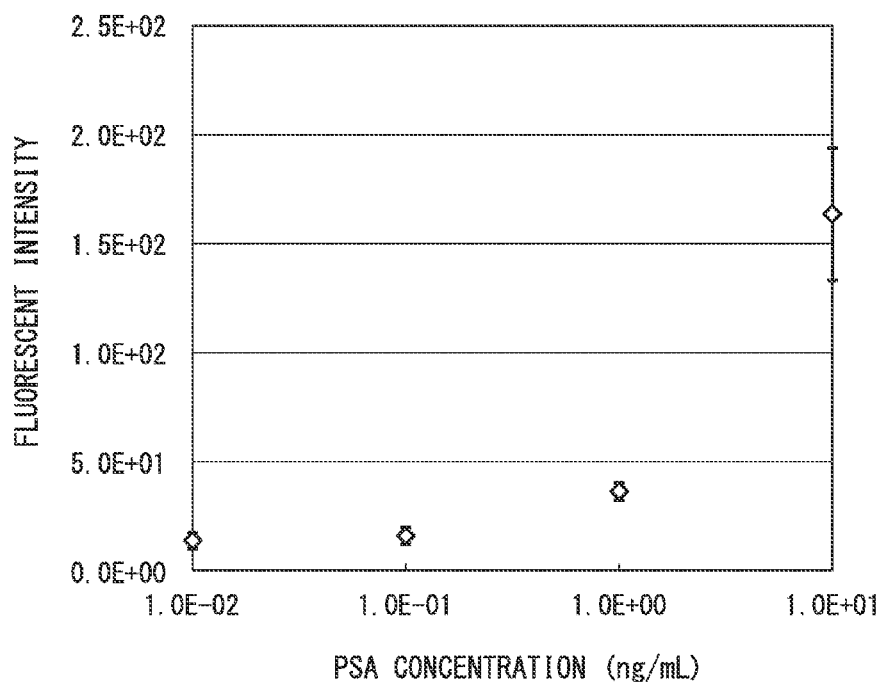
FIG. 5 is an example of an experimental result of the detection system.

A test strip was prepared using the membrane, the coupled pad, a water absorbing pad, and a sample pad. Antigen solutions at each of concentrations (PSA concentrations: 0 ng/mL, 0.01 ng/mL, 0.1 ng/mL, 1 ng/mL, and 10 ng/mL) were added dropwise to test strips. After the lapse of 15 minutes, fluorescent color development of the magnetic particle for marking at the test line position was detected using fluorescent Immunochromato-Reader, and digitization was performed. The results are shown in FIG. 5.

With the results from Example 2, it was confirmed that there was concentration dependency in the fluorescent intensity with respect to the antigen concentration. It was confirmed that the test substance was detected by the magnetic accumulation using the medium between glasses with a gap, the magnetic particle, and the marking particle. In regards to the detection limit, no detection was confirmed at a concentration lower than or equal to 0.01 ng/mL in calculation through a 2-SD method. For this reason, the detection limit (detection lower limit) was in a range of 0.01 to 0.1 ng/mL.

On the other hand, in regards to the detection limit in Comparative Example 1, the detection limit (detection lower limit) was in a range of 0.1 to 1 ng/mL in calculation through a 2-SD method.

As described above, in the detection system of a test substance of the present invention, in the detection through the magnetic accumulation using the medium between glasses with a gap, the magnetic particle, and the marking particle, it was confirmed that the detection limit was in a lower concentration region than the detection using a general test strip. In addition, it became possible to detect an antigen (PSA) at a low concentration which was impossible to detect in the general immunochromatography, through the detection system of a test substance of the present invention.

What is claimed is:

1. A detection system for detecting a test substance, comprising:
a magnetic body that is modified by a first substance capable of being bound to a test substance at a first binding site of the test substance;
a marker that is modified by a second substance capable of being bound to the test substance at a second binding site of the test substance, the second binding site being a different site from the first binding site;
a development medium having
a first sheet with light transparency, the first sheet having a first plane surface,
a second sheet with light transparency, the second sheet being arranged in parallel with the first sheet, the second sheet having a second plane surface arranged so as to face the first plane surface, the second sheet being arranged so that an entire surface of the second plane surface is arranged in parallel with the first plane surface,
a flow passage provided between the first plane surface and the second plane surface, the flow passage being constructed by the first plane surface, the second plane surface, and a cavity divided by the first plane surface and the second plane surface so as to have a gap between the first plane surface and the second plane surface, the flow passage having the gap into which liquid, in which the magnetic body and the marker is dispersed, flows by a capillary phenomenon, and a detection position to detect the marker in a portion of the flow passage, the development medium having light transparency at least in the detection position; and a magnetic force generating portion that is equipped in the development medium in order to hold the magnetic body in a portion of the flow passage.

2. The detection system according to claim 1, further comprising:

a detection device to detect light emitted from the inside of the flow passage, wherein the marker has a dye.

3. The detection system according to claim 2, wherein the detection device comprises:

a light source which emits light containing excitation light having a predetermined wavelength;

a light passage member which irradiates the flow passage with the excitation light;

a filter which removes the excitation light; and a detection portion which detects light transmitted through the filter, wherein the marker is marked by a fluorescent substance, which emits fluorescence by the excitation light.

4. The detection system according to claim 1, wherein the first substance is selected from a group consisting of an antibody, a fragmented antibody, a complete antigen, a hapten, and an aptamer.

5. The detection system according to claim 1, wherein the second substance is selected from a group consisting of an antibody, a fragmented antibody, a complete antigen, a hapten, and an aptamer.

6. The detection system according to claim 1, wherein the marker contains a marking substance selected from a group consisting of a colorimetric substance, a luminescent substance, an enzyme coloring substance, and an oxidation-reduction substance.

7. The detection system according to claim 2, wherein the detection device is disposed in the detection position such that the detection device faces the magnetic force generating portion through the development medium.

8. The detection system according to claim 2, further comprising:

stirring particles configured to stir the liquid in the flow passage.

* * * * *